United States Patent [19]

Michelson

[11] Patent Number: 4,959,058
[45] Date of Patent: Sep. 25, 1990

[54] CANNULA HAVING SIDE OPENING

[76] Inventor: Gary K. Michelson, 438 Sherman Canal, Venice, Calif. 90291

[21] Appl. No.: 341,850

[22] Filed: Apr. 24, 1989

Related U.S. Application Data

[63] Continuation-in-part of Ser. No. 324,727, Mar. 17, 1989.

[51] Int. Cl.⁵ .............................................. A61M 25/00
[52] U.S. Cl. ........................................ 604/280; 128/4
[58] Field of Search ............... 604/280, 283, 264, 268, 604/272; 128/4

[56] References Cited

U.S. PATENT DOCUMENTS 4,857,057 8/1989 Sanagi ...................................... 128/4
4,867,747 9/1989 Yarger ...................................... 128/4

Primary Examiner—John D. Yasko
Attorney, Agent, or Firm—Lewis Anten

[57] ABSTRACT

A tubular cannula for use with an arthroscope consisting of a protective tubular sleeve for surrounding the arthroscope, the sleeve having a narrow diameter portion slightly larger than the diameter of the arthroscope at its lower end for supporting the arthroscopic viewing element is disclosed. A series of openings, in the form of slots are located along the side of the cannula near the point of transition from the normal diameter to the narrow diameter for permitting the flow of fluids between the inside wall of the cannula and the outside wall of the arthroscope.

10 Claims, 2 Drawing Sheets

CANNULA HAVING SIDE OPENING

RELATED APPLICATIONS

This is a continuation in part of the copending application for a cannula entitled, IMPROVED CANNULA FOR AN ARTHROSCOPE filed Mar. 17, 1989, Ser. No. 324 by Gary Karlin Michelson, M.D.

BACKGROUND

Endoscopes are slender light transmitting glass lined metal rods used during operations to permit the doctor to see within the site of the operation, such as during an arthroscopic procedure. Endoscopes designed and dimensioned for use in the joints of the body are referred to as arthroscopes. Since arthroscopes are very expensive, typically many thousands of dollars, and are very fragile, they are carefully protected by an outer cannula. A cannula is a tubular sleeve like member that closely surrounds the arthroscope, mitigating against breakage, during introduction into the wound or during use.

During an operation, it is necessary in order for the surgeon to see within the operating space for fluid to be introduced into the site of the operation to both inflate the site of the operation and to make sure that clear fluid is in the site. This is typically achieved by having an inlet at the proximate end of the cannula which forces sterile water through the space between the inside wall of the cannula and the outer wall of the arthroscope and into the wound. If the fluid becomes cloudy, then the inlet is closed and suction can be applied to an outlet at the proximate end to withdraw the cloudy fluid.

However, because of the close tolerances required to support the arthroscope, the volumetric space between the cannula wall and the arthroscope is very limited, and can not be arbitrarily increased If too much clearance is provided, then the support to the arthroscope may be insufficient to prevent its breakage. Further, the size of the cannula can not be substantially increased due to the inability to maneuver a substantially larger instrument into the operation site. Thus, when substantial amounts of fluid must be introduced into the operation site and insufficient flow is obtainable through the arthroscope and cannula device, it is then necessary to introduce the fluid through additional incisions made into the site. While this is undesirable in any case, in some procedures, such as an arthroscopic procedure on the shoulder, the additional incisions could cause real damage to the rotator cuff. At the same time, the presence of additional tubes cause the procedure itself to be more difficult to perform. Thus, the design of the prior cannula represented a compromise between the desire to adequately support the arthroscope and the desire to have fluid flow.

Also, in the prior cannula devices, the suction of the fluids and other materials were sucked up against the viewing element of the arthroscope since the access was proximate the viewing element. Once clogged, the arthroscope had to be removed.

SUMMARY OF THE INVENTION

A tubular cannula for use with an arthroscope consisting of a protective tubular sleeve for surrounding and supporting the arthroscope. The sleeve has a narrow diameter portion at its lower end for directly supporting the arthroscopic viewing element. A series of openings, in the form of slots, are located along the side wall of the cannula proximate the transition to the narrow portion for permitting the flow of fluids into the cannula into the space between the inside wall of the cannula and the outside wall of the arthroscopic viewing element.

The small diameter portion at the lower end of the cannula permits the arthroscope to be inserted into smaller spaces within the joint during operations than possible with previously available devices. The narrow diameter portion of the sleeve also firmly supports the end of the viewing element and permits the remainder of the sleeve to have a normal, or even greater than normal diameter without compromising the support needed for the viewing element. This increases the cross sectional flow area compared to conventional arthroscopes. Since fluid flow in a tubular member increases to the fourth power as the diameter increases, the fluid flow of the system is significantly greater than previously available.

The viewing element can be additionally supported by means of projections extending from the inside wall of the cannula to support the arthroscopic viewing element along points intermediate its ends, as disclosed in the applicant's copending application referred to above. In the present invention the fluid access is away from the viewing element and therefore the viewing element does not get covered during the suction procedure.

OBJECTS OF THE PRESENT INVENTION

It is an object of the present invention to provide for a cannula that is more reliable;

It is another object of the present invention to provide a cannula that is more useful during operations;

It is another object of the present invention to provide a cannula that is less likely to break;

It is yet another object of the present invention to provide a cannula that permits better viewing and access to small locations;

It is another object of the present invention to provide a cannula that permits increased fluid flow;

It is still another object of the present invention to provide a cannula that is less likely to clog or block the field of view;

These and other objects of the present invention will be apparent from a review of the following specification and the accompanying drawings.

DETAILED DESCRIPTION OF THE DRAWINGS

Figure 1:
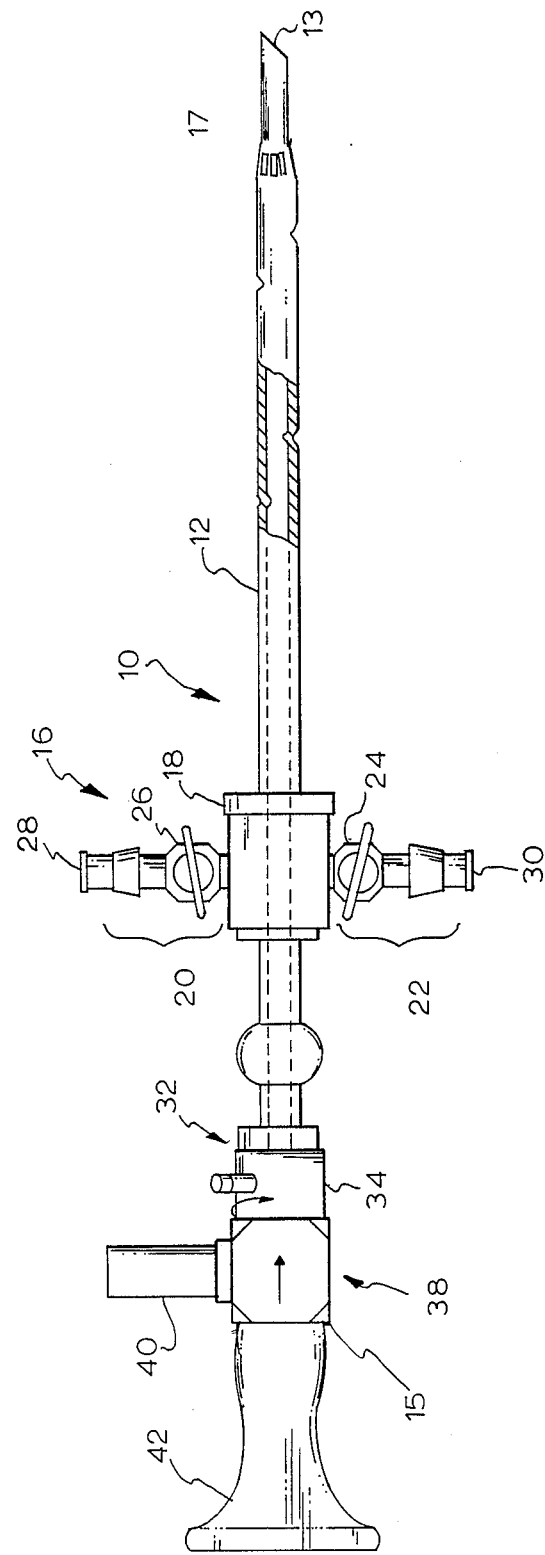
FIG. 1 is a partial sectional side elevational view of an arthroscopic cannula with the arthroscope fully inserted.
Figure 2:
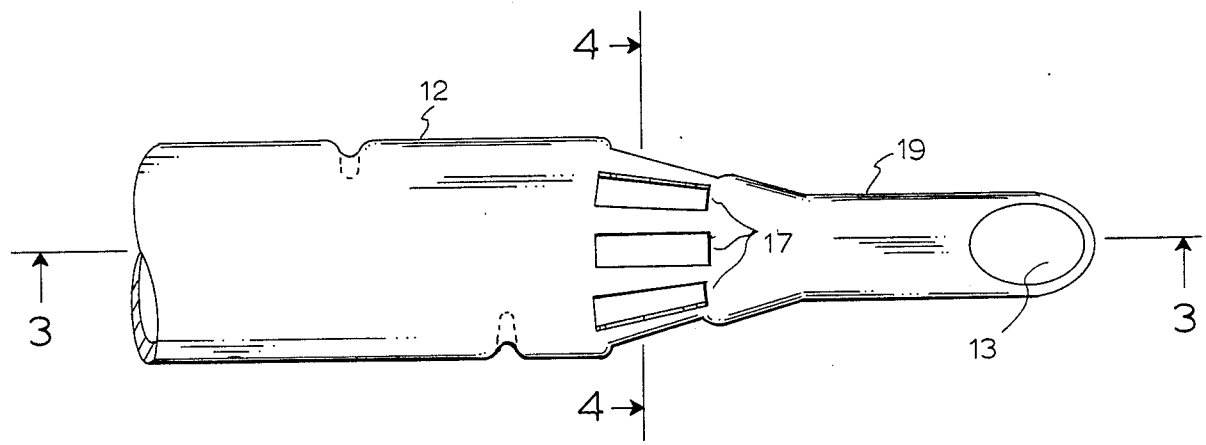
FIG. 2 is an expanded side view of the cannula of FIG. 1.

Referring to FIG. 1 there is shown a cannula 10 constructed in accordance with the present invention. FIG. 1 shows the arthroscope 38 coupled to the cannula 10. The arthroscope 38 is of standard design and construction with the usual input light connection 40 and viewing eyepiece 42 typically connected to a television camera (not shown).

The cannula 10 consists of an elongated hollow tubular member 12 having a viewing end 15 and a distal end 13. The distal end 13 is beveled and slotted 17 to enable the arthroscope 38, which also has a beveled end, to have a clear field of view during use. The diameter of the distal end 13 is a narrowed diameter portion 19 having a length of about 1 cm. The juncture from the tubular member 12 to the narrowed portion 19 has a series of openings 17. In the preferred embodiment, the openings 17 are in the form of slots approximately 1.5 mm wide and 5 mm long. With an arthroscope having an inside diameter of 4 mm in the narrowed portion and an inside diameter of 5.5 mm in the narrowed portion, with a wall thickness of about 0.5 mm, twelve equally spaced openings 17 can be employed.

Proximate the viewing end 15 of the cannula 10 a bypass fitting 16 is provided which includes a collar 18 mounting opposed nipples 20, 22. Each fitting includes an in-line valve 24, 26 for selective closure and fittings 28, 30 for attachment to fluid carrying hoses (not shown).

The arthroscope 38 is removably attached to a coupling member 32, typically by a bayonet arrangement.

Figure 3:
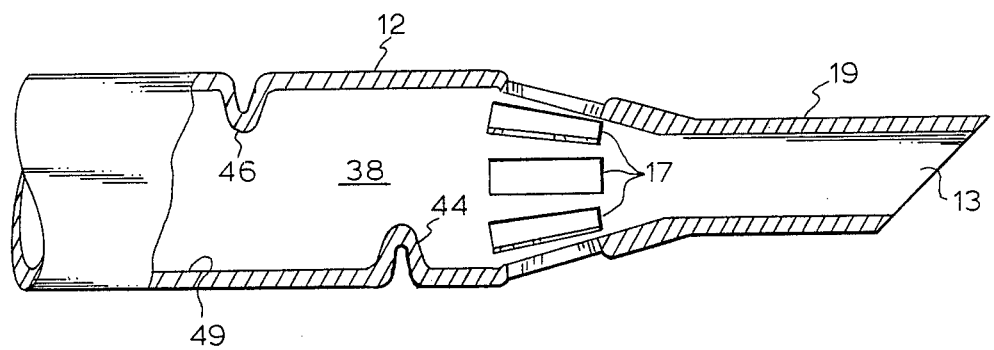
FIG. 3 is a side sectional view of the cannula of FIG. 2 taken along lines 3—3.
Figure 4:
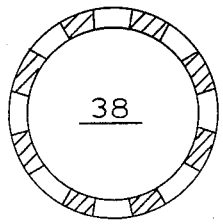
FIG. 4 is a cross sectional view of the end of the cannula taken along lines 4—4 of FIG. 2.

Referring to FIGS. 3 and 4 the internal structure of the cannula 10 is shown supporting an arthroscopic element 38. The inside of the tubular member 12 has a plurality of longitudinal support segments 44, and 46 of uniform cross-section, projecting radially inwardly from the inner cannula wall 49 to just touch the arthroscopic viewing element 38. Substantial space is created between the outside wall of the arthroscopic element 38 and the inner wall 49 of the cannula 10. The support segments 44 and 46, are formed by any number of means, such as corrugating the tubular member 12 or by creating depressions or dimples in the tubular member 12.

The arthroscope is supported by the cannula at both of its ends, even if the supporting projections 44 are not employed. With the supporting projections 44, the arthroscope element is firmly supported at both ends and at intermediate points. The use of the narrowed portion 19, and the supporting projections 44 allows the use of a decreased wall thickness without compromising the support and protection afforded to the arthroscope.

The device of the present invention is used in the same manner as a conventional cannula and arthroscope. An incision is made and an obdurator is inserted into the cannula 10. The obdurator projects slightly beyond the distal end of the cannula 10 and pushes through the soft tissue, gaining entrance for the cannula 10. Once inserted in place, the obdurator is removed, leaving the cannula in place The arthroscope is then introduced into the cannula 10 and locked in place. The tubing is then attached to the inlet 28 and outlet 30. As a result of the larger volumetric space created in the cannula, there is increased capacity for the inflow and outflow of fluids.

While the above invention has been described with regards to its use with an arthroscope, it is recognized that the present inventive concept could be used with endoscope devices in general. Also, it is appreciated that variations of the construction of the cannula and the means of forming the projections can be made without departing from the present inventive concept disclosed.

What is claimed is:

1. A cannula for use with an endoscopic surgical instrument comprising:
a hollow tubular member defining an inside and an outside for surrounding an endoscopic element, said hollow tubular member having a first diameter portion and a second narrow diameter supporting portion having a diameter narrower than the inside diameter of said first diameter portion proximate one end of said hollow tubular member for supporting an endoscopic element with said cannula, said narrow diameter portion in close fitting, free sliding engagement with said endoscopic element, and openings through said hollow tubular member permitting the flow of fluid through said openings from the inside of said cannula to the outside of said cannula.

2. The device of claim 1 in which said hollow tubular member has a circular cross section.

3. The device of claim 1 in which at least a portion of said first diameter portion of said hollow tubular member is corrugated along the longitudinal axis of said hollow tubular member.

4. The device of claim 1 in which at least one support means in the form of an extension extends inwardly from the inner wall of said first diameter portion of said hollow tubular member for supporting an endoscopic element.

5. The device of claim 1 in which said support means comprise a plurality of dimples extending inwardly into close fitting relation with the outer wall of an arthroscopic element.

6. The device of claim 1 in which there is a transition portion from said second narrow diameter portion to said first diameter portion said opening located proximate said transition portion.

7. The device of claim 6 in which said openings are longitudinal slots.

8. A hollow cannula for use with an arthroscope of the type including a cannula for housing and protecting the arthroscope comprising an arthroscope and a cannula surrounding said arthroscope,
said cannula having a first diameter portion and a second narrower diameter portion at one end of said cannula, said second narrower diameter portion supporting said arthroscope, said narrow diameter portion in close fitting, free sliding engagement with said arthroscope, and openings through said tubular member permitting the flow of fluid through said openings from the inside of said cannula to the outside of said cannula.

9. The cannula of claim 1 in which the space between the wall of said cannula and the outside wall of the arthroscope is not uniform in cross section.

10. The device of claim 1 in which the inside diameter of the second narrow diameter portion is approximately 4 mm, and the inside diameter of the first diameter portion is approximately 5.5 mm.

* * * * *